(12) United States Patent
Sahai

(10) Patent No.: US 6,654,631 B1
(45) Date of Patent: Nov. 25, 2003

(54) METHOD AND APPARATUS FOR A HAND-HELD COMPUTER EKG DEVICE

(76) Inventor: Anil Sahai, 709 White Post Dr., Webster City, IA (US) 50595

(*) Notice: Subject to any disclaimer, the term of this patent is extended or adjusted under 35 U.S.C. 154(b) by 223 days.

(21) Appl. No.: 09/904,336

(22) Filed: Jul. 12, 2001

(51) Int. Cl.$^7$ .............................................. A61B 5/0402
(52) U.S. Cl. ........................ 600/509; 600/523; 600/513; 128/903
(58) Field of Search ................................ 600/508, 509, 600/520, 522, 523, 513; 128/903, 904

(56) References Cited

U.S. PATENT DOCUMENTS

| | | | | |
|---|---|---|---|---|
| 5,417,222 A | * | 5/1995 | Dempsey et al. | 600/509 |
| 5,682,902 A | * | 11/1997 | Herleikson | 600/521 |
| 5,876,351 A | * | 3/1999 | Rohde | 600/523 |
| 6,149,602 A | | 11/2000 | Arcelus | |
| 6,526,310 B1 | * | 2/2003 | Carter et al. | 600/509 |
| 6,549,756 B1 | * | 4/2003 | Engstrom | 455/66 |

* cited by examiner

Primary Examiner—Jeffrey R. Jastrzab
(74) Attorney, Agent, or Firm—McKee, Voorhees & Sease, P.L.C.

(57) ABSTRACT

A method and system for hand-held medical monitoring is disclosed. The system includes a plurality of EKG capable electrodes, and analog digital converter electrically connected to the plurality of electrodes and having a plurality of channels, a control circuit electrically connected to the analog digital converter, a serial transceiver electrically connected to the control circuit, a first hand-held personal digital assistant electrically connected to the serial transceiver and adapted for wireless communication, and a set of instructions stored on the first hand-held personal digital assistant for receiving measurements from the plurality of electrodes and displaying measurements from one or more of the plurality of electrodes and wirelessly transmitting measurements from one or more of the plurality of electrodes. Preferably, the system and method also provide for a remote hand-held personal digital assistant and wireless contact with the first hand-held personal digital assistant and adapted for remotely receiving the measurements from the first hand-held personal digital assistant and displaying the measurements.

13 Claims, 4 Drawing Sheets

```
WHILE (TRUE) LOOP
    FOR i = 1 TO 12
        RECEIVE ELECTRODE CHANNEL (i);
        TRANSMIT ELECTRODE CHANNEL (i);
        DISPLAY CHANNEL (i);
    NEXT:
    RECEIVE (OXYGEN-SENSOR);
    DISPLAY (OXYGEN-SENSOR);
    TRANSMIT (OXYGEN-SENSOR);
END LOOP
```

*Fig. 4*

METHOD AND APPARATUS FOR A HAND-HELD COMPUTER EKG DEVICE

BACKGROUND OF THE INVENTION

1) Field of the Invention

The invention relates to the field of hand-held medical monitoring. More particularly, but not exclusively, the invention relates to a hand-held computer adapted for EKG measurements.

Numerous attempts have been made at medical monitoring. Prior art devices for medical monitoring, including electrocardiographs. An electrocardiograph is an instrument used in the detection and diagnosis of heart abnormalities that measures electrical potentials on the surface of a body and is capable of generating a record of electrical currents associated with the heart muscles activities.

2) Problems With the Art

One problem associated with electrocardiographs (EKG) is the high cost of such units. Due to the high costs of EKGs, they are not always available where they could be used. Some emergency response units and other first responders do not have EKG units available. When EKG units are available to first responders, valuable, potentially life saving, information can be determined prior to the patient's arrival at a medical facility.

A further problem with the use of EKGs by first responders is that the first responders are normally not fully qualified to evaluate a patient's medical condition from reading an EKG. Therefore, even if an emergency responder had an EKG available to them, such as in an ambulance, the EKG could not be used in a manner that would help the patient in the most effective way.

This is particularly true where the EKG is configured to have more than a minimum number of leads. For example, the EKG can have twelve leads. Not all emergency response units are equipped with a twelve lead EKG. There are substantial benefits to using a twelve-lead system in prehospitalization care. For example, a twelve lead EKG may detect certain conditions that although initially experienced by the patient are not detectable later. One example of such a transient condition is ischemia. This decrease in the blood supply to the heart is best detected immediately at the time of transport of the patient rather than later at a hospital where the condition may no longer be detectably present. Therefore, monitoring using an EKG at the time of first response is beneficial, but has not yet been fully adopted.

Further, even when EKG monitoring takes place at the site of the first response or in transit to a hospital, the information that is collected is not necessarily used. Currently, an EKG trace can be transmitted to a hospital via specialized equipment. This equipment may be cost prohibitive. Further, there is no guarantee that there is a doctor at the hospital that is free to monitor the EKG received by the hospital.

Therefore problems regarding EKG units remain.

It is therefore an object, feature, or advantage of the present invention to provide for a hand-held medical monitoring device.

It is a further object, feature, or advantage of the present invention to provide a hand-held medical monitoring device that performs the function of an EKG.

A further object, feature, or advantage of the present invention in the provision of an EKG device capable of using 10 electrodes to provide 12 lead EKG.

A still further object, feature, or advantage of the present invention is to provide an EKG device capable of wirelessly transmitting measurements to a medical professional.

It is a further object, feature, or advantage of the present invention to provide a hand-held medical monitoring device capable of sensing oxygen levels in a patient.

It is a further object, feature, or advantage of the present invention to provide a hand-held medical monitoring system that may be used to remotely monitor medical conditions of a patient.

A further object, feature, or advantage of the present invention to provide for a hand-held medical monitoring device that is low cost.

Yet another object, feature, or advantage of the present invention is to provide a system for hand-held medical monitoring that a doctor to remotely monitor medical conditions with patient from any location.

It is a further object, feature, or advantage of the present invention to provide a system for hand-held medical monitoring that allows a doctor to remotely monitor a patient without requiring highly expensive and specialized equipment.

As a further object, feature, or advantage of the present invention to provide a hand-held medical monitoring device that is capable of improving the quality of prehospitalization care.

These and other objects, features, and advantages of the present invention will become more apparent from the specification and claims.

BRIEF SUMMARY OF THE INVENTION

One aspect of the present invention is a system for hand-held medical monitoring. The system comprises a plurality of EKG capable electrodes, an analog to digital converter electrically connected to the plurality of electrodes and having a plurality of channels, a control circuit electrically connected to the analog to digital converter, a serial transceiver electrically connected to the control circuit, a hand-held personal digital assistant electrically connected to the serial transceiver and adapted for wireless communication, and a set of instructions stored on the hand-held personal digital assistant for receiving measurements from the plurality of electrodes and displaying measurements from the plurality of electrodes and wirelessly transmitting measurements from one or more of the plurality of electrodes. The system allows for hand-held medical monitoring including both EKG functions as well as an optional function for measuring oxygen saturation. The invention allows for a plurality of electrodes to be used, including a 10 electrode configuration. The personal digital assistant of the present invention is programmed to receive, display, and store the EKG measurements and optionally the oxygen saturation measurements.

According to the system of the invention, a remotely located personal digital assistant can be used. The remote personal digital assistant is programmed to wirelessly receive information from the hand-held personal digital assistant that is connected to a patient. On the remote personal digital assistant, the same information displayed and/or stored on the first personal digital assistant may be displayed and/or stored.

Another aspect of the present invention involves a method for hand-held medical monitoring. The method includes transducing a plurality of EKG signals in a corresponding plurality of EKG electrodes adapted for coupling to a human body, converting the EKG signals to a digital signal using an analog to digital converter having multiple channels, receiving the digital signal at a first hand-held personal digital assistant adapted for wireless communication, displaying EKG measurements corresponding to the EKG electrodes on the screen of the first hand-held personal digital assistant, wirelessly transmitting the EKG measurements, wirelessly receiving the transmitted EKG measurements on a second personal digital assistant, and displaying the EKG measurements on the second personal digital assistant.

The present invention is particularly advantageous where a first responder can connect the device to a patient and then transmit the readings to a remote personal digital assistant such as a doctor may have available, no matter where they are located. The doctor can then evaluate the condition of the patient prior to the patient's arrival at a medical facility.

BRIEF DESCRIPTION OF THE DRAWINGS

FIG. 4 is pseudo code for one method of the present invention.

DETAILED DESCRIPTION OF AN EXEMPLARY EMBODIMENT

Figure 1:
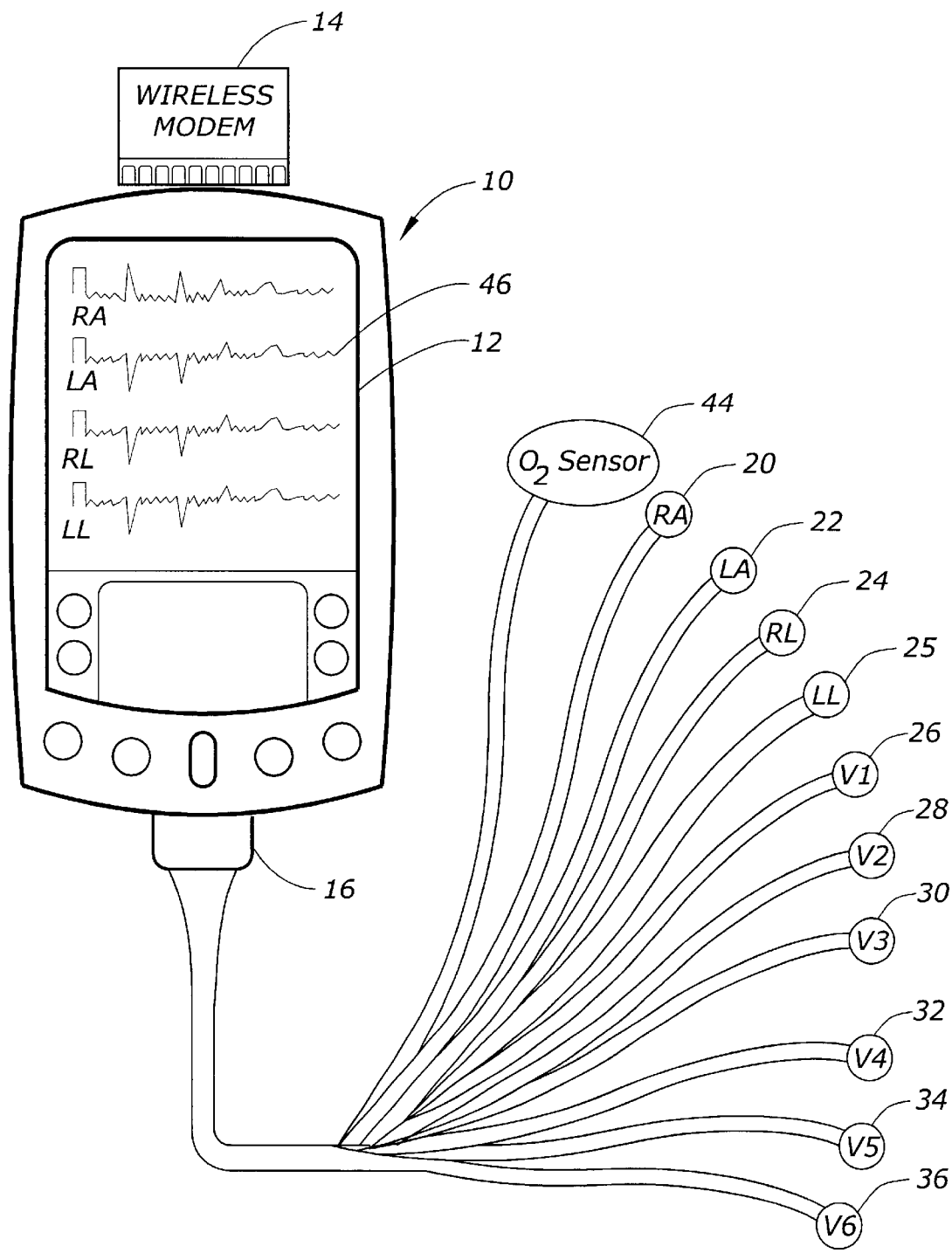
FIG. 1 is a diagram of a hand-held personal digital assistant configured for medical monitoring of the present invention.

The present invention provides for a system and method of medical monitoring using a hand-held computer EKG device. FIG. 1 illustrates the medical monitoring device 10. The medical monitoring device 10 includes a PDA portion 12. The PDA 12 is preferably a 3com palm pilot although the present invention contemplates that other types of personal digital assistants may be used. For example, the present invention contemplates that PDA's available from Visor as well as Windows CE capable PDA's may be used. One advantage of the present invention is that it allows off the shelf PDA's to be used for medical monitoring.

The hand-held medical monitoring device 10 may also be configured for wireless communications such as through a wireless modem 14. The present invention contemplates that the PDA 12 may be configured for wireless operation in various ways, including using a wireless modem, having wireless capability built-in or other variations such as may be known in the art. In addition, the hand-held medical monitoring device 10 includes an interface 16. The interface 16 allows multiple medical monitoring sensors to be electrically connected to the PDA 12. Preferably, 10 lead EKG sensors may be connected. Electrodes RL, LL, RA 24, V1 26, V2 28, V3 30, V4 32, V5 34, V6 36, and LA may be connected. The present invention allows for fewer numbers of electrodes to be used such as in a four-lead system, however, preferably a 10 electrodes EKG is used.

The PDA 12 receives measurements through the interface 16 and is programmed to display the measurements such as by visually displaying standard EKG tracings on the display 46.

The present invention contemplates that the PDA 12 may display various formats of information on a display 46. The present invention contemplates that the PDA 12 supports both basic functions and advance functions. Basic functions include display in the data, display a selection function displaying arrangement, displaying of page on the screen, allowing cursor movement and mode changes by the operator, displaying a continuous rhythm strip, and performing basic data analysis. Advance functions of the present invention include the ability to zoom in on a portion of the data display, making measurements on the screen, comparing the measurements with stored data, detecting patterns in the data that may be useful for diagnosis purposes, performing other analysis which may be useful for diagnosis purposes, and providing additional interpretation. The present invention is not, however, limited to just these functions.

Figure 2:
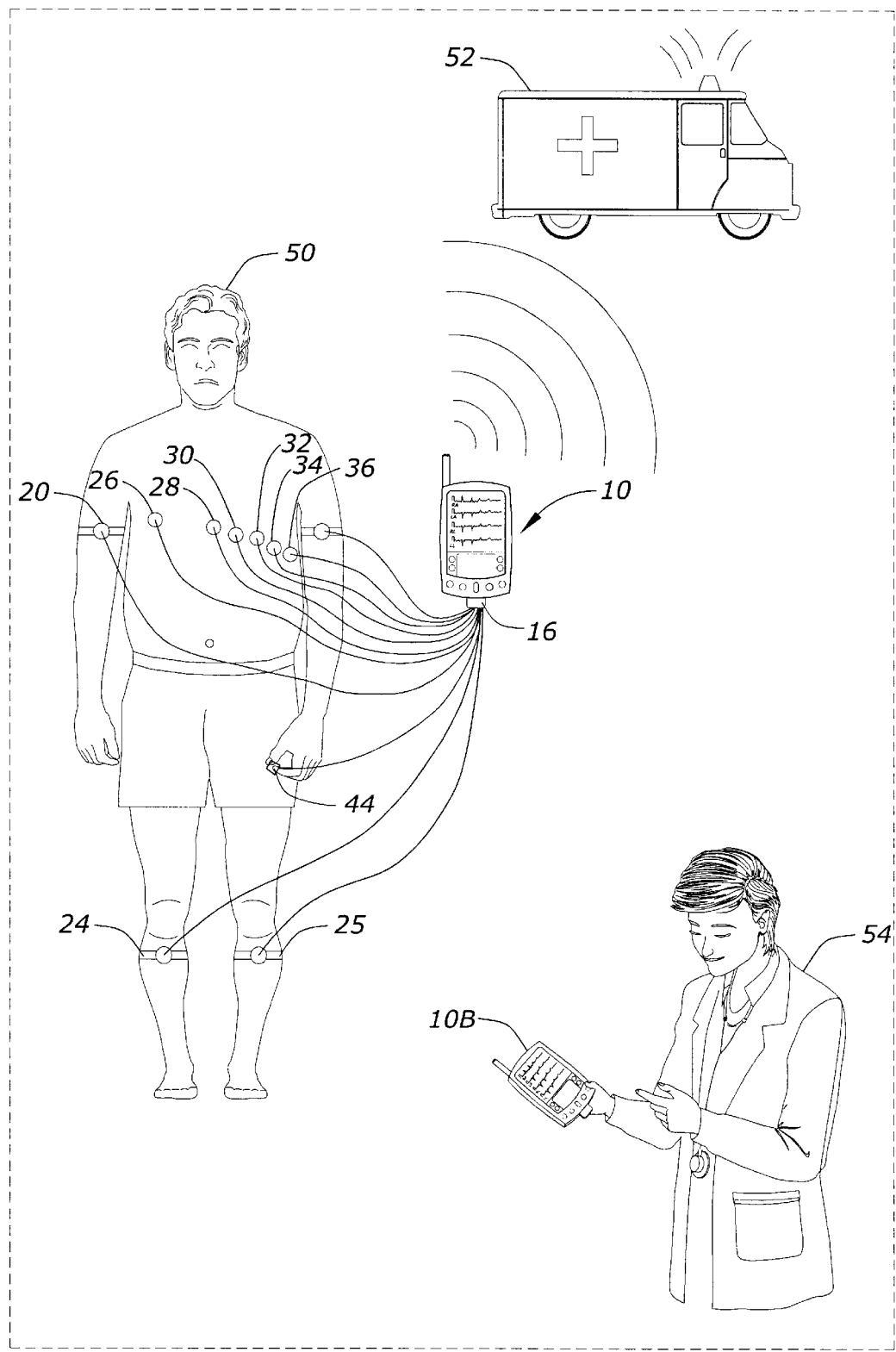
FIG. 2 is a diagram showing a system of the present invention.

FIG. 2 illustrates the system and method of the present invention. In FIG. 2 a patient 50 is shown. A first responder unit 52 is at the side of patient 50. The emergency response personnel can then connect the electrodes of the EKG to the patient 50. In addition, the oxygen sensor 44 such as a pulse oximeter can be connected to the patient. The hand-held PDA for medical monitoring 10 then displays the measurements obtained from the patient 50 and transmits these measurements to a remote PDA 10B. A doctor 54 or other qualified medical professional can then view the same measurements including the same tracings that are available to the first response team. This allows the doctor or other qualified care provider to assess the patient's condition prior to being able to physically examine the patient. This improves the quality of medical services received by the patient, decreases the amount of time before a doctor's expertise can be relied upon in patient care, as well as providing other advantages.

Figure 3:
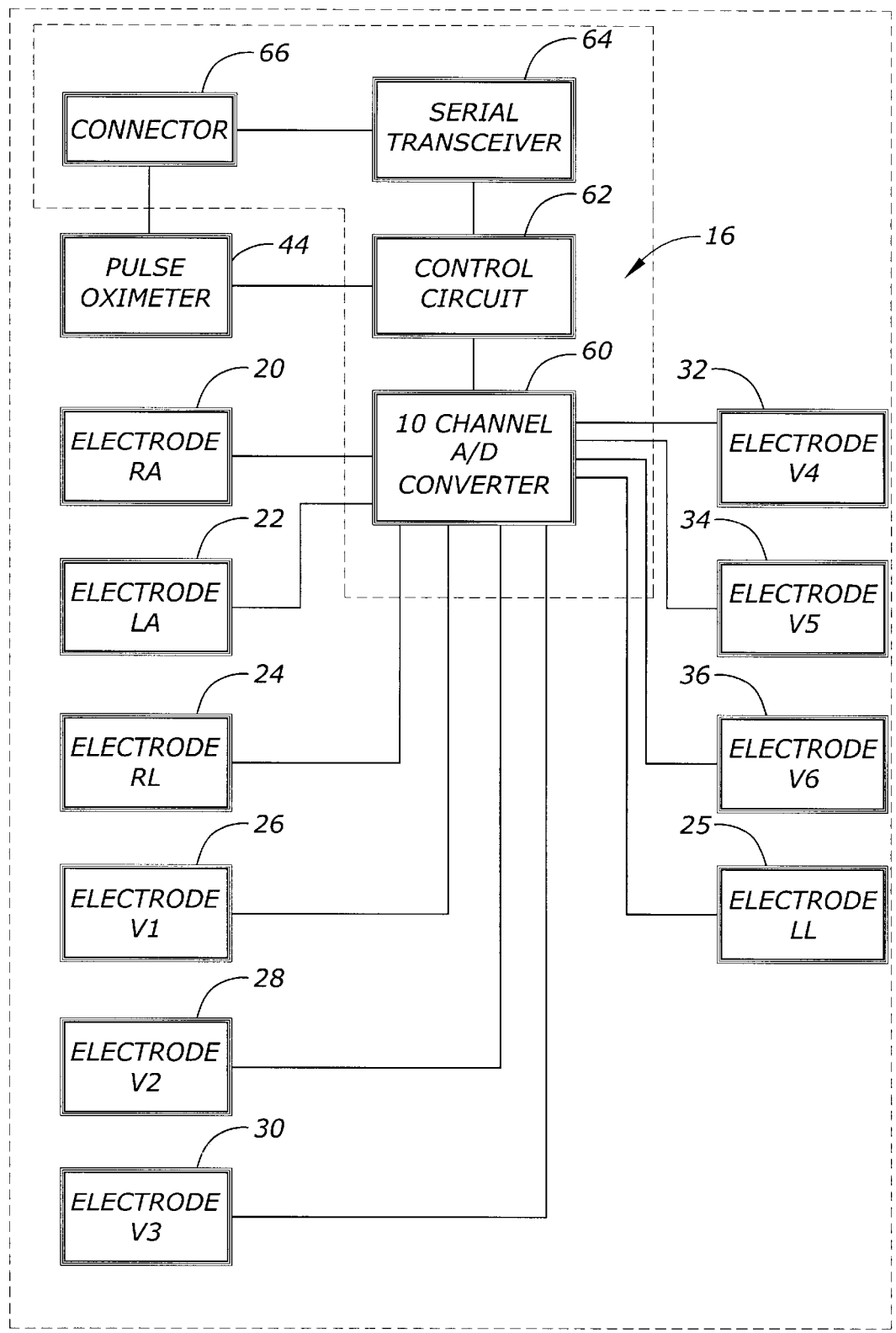
FIG. 3 is a block diagram of the medical monitoring unit of the present invention.

FIG. 3 displays a block diagram of the interface 16 of the present invention as it is electrically connected to a plurality of sensors. In FIG. 3, a connector 66 is used to connect to the PDA. The present invention contemplates that different types of connectors may be used. One convenient type is a serial connection. Either an RS-232C serial connection or a USB serial connection can be used, as these types of interfaces are relatively standard on personal digital systems. However, the present invention contemplates that other types of interfaces may be used as may be appropriate for a particular PDA or in a particular environment or otherwise desirable. The connector is electrically connected to a serial transceiver 64, which is electrically connected to a control circuit 62. The control circuit 62 is electrically connected to an A/D converter 60. Where a twelve-lead EKG system is used, the 10 twelve separate channels, one for each electrode. The present invention contemplates that other types of A/D converters may be used particularly where different numbers of leads are used. The A/D converter 60 is connected to each of the electrodes, including electrodes RA, RL, LA, LL, V1, V2, V3, V4, V5 and V6.

The invention also provides for use of an oxygen saturation sensor such as a pulse oximeter 44. As pulse oximeters often have digital controls, the pulseoximeter 44 is electrically connected directly to the control circuit 62. The present invention contemplates that the electronics of the interface 16 may be implemented using an integrated circuit, or a circuit containing an intelligent control such as a microprocessor, microcontroller, or digital signal processor. The present invention further contemplates that the control circuit 62 and the A/D converter 60 may be a part of the same intelligent control.

FIG. 4 illustrates pseudo code for the PDA 12 of the present invention. The PDA is programmed to receive information from the electrodes on each of the channels. Then this information may be transmitted to a remote location and may be displayed. Similarly, measurements from an oxygen saturation sensor may be measured, displayed, transmitted. The present invention contemplates that various orders of operations may be used to effect the same or similar results. Where a remote PDA is used to receive the information, the remote PDA may be programmed in the same way to receive measurements across a communications channel and display these measurements.

A system and method for hand-held medical monitoring has now been disclosed. The present invention contemplates numerous other variations within the spirit and scope of the invention.

What is claimed is:

1. A system for hand-held medical monitoring comprising:
    an interface comprising a plurality of EKG capable electrodes, an analog to digital converter electrically connected to the plurality of electrodes and having a plurality of channels, a control circuit electrically connected to the analog to digital converter, and a serial transceiver electrically connected to the control circuit;
    a first hand-held personal digital assistant removably connected to the interface through a serial connection electrically connected to the serial transceiver, the first hand-held personal digital assistant being adapted for wireless communication and having a display; and
    a set of instructions stored on the first hand-held personal digital assistant for receiving measurements from the plurality of electrodes and displaying measurements from one or more of the plurality of electrodes and wirelessly transmitting measurements from one or more of the plurality of electrodes to a remote location.

2. The system for hand-held medical monitoring of claim 1 further comprising an oxygen sensor electrically connected to the control circuit for measuring oxygen saturation.

3. The system of claim 1 wherein the plurality of electrodes is 10 electrodes and the plurality of channels is at least 12 channels.

4. The system of claim 1 further comprising a second set of instructions stored on the first hand-held personal digital assistant for wirelessly receiving a second set of EKG measurements and displaying the second set of EKG measurements.

5. The system of claim 1 further comprising a remote hand-held personal digital assistant in wireless contact with the first hand-held personal digital assistant and adapted for remotely receiving the measurements from the first hand-held personal digital assistant and displaying the measurements.

6. A method for hand-held medical monitoring comprising:
    transducing a plurality of EKG signals in a corresponding plurality of EKG electrodes coupled to a human body;
    converting the EKG signals to a digital signal using an analog to digital converter having multiple channels;
    receiving the digital signal in a first hand-held personal digital assistant adapted for wireless communication;
    displaying EKG measurements corresponding to the EKG electrodes on a screen of the first hand-held personal digital assistant;
    wirelessly transmitting the EKG measurements;
    wirelessly receiving the transmitted EKG measurements on a second personal digital assistant at a remote location; and
    displaying the EKG measurements on the second personal digital assistant.

7. The method of claim 6 further comprising measuring an oxygen saturation signal; wirelessly transmitting the oxygen saturation measurement; receiving the transmitted oxygen saturation measurement on a second personal digital assistant; and displaying the transmitted oxygen saturation measurement on the second personal digital assistant.

8. The method of claim 6 wherein the plurality of EKG electrodes is 10 EKG electrodes.

9. A system for hand-held medical monitoring comprising:
    a plurality of EKG capable electrodes;
    an interface having an analog to digital converter electrically connected to the plurality of electrodes and having a plurality of channels and a control circuit electrically connected to the analog to digital converter;
    a first hand-held personal digital assistant electrically connected to the interface and adapted for wireless communication;
    a set of instructions stored on the first hand-held personal digital assistant for receiving measurements from the plurality of electrodes and displaying measurements from one or more of the plurality of electrodes and wirelessly transmitting measurements from one or more of the plurality of electrodes; and
    a remote hand-held personal digital assistant in wireless contact with the first hand-held personal digital assistant and adapted for remotely receiving the measurements from the first hand-held personal digital assistant and displaying the measurements.

10. The system for hand-held medical monitoring of claim 9 further comprising an oxygen sensor electrically connected to the control circuit for measuring oxygen saturation.

11. The system of claim 9 wherein the plurality of electrodes is 10 electrodes and the plurality of channels is at least 12 channels.

12. The system of claim 9 further comprising a second set of instructions stored on the first hand-held personal digital assistant for wirelessly receiving a second set of EKG measurements and displaying the second set of EKG measurements.

13. A method for remote medical monitoring, comprising:
    transducing a plurality of EKG signals from a corresponding plurality of EKG electrodes coupled to a human body;
    displaying a representation of the EKG signals on a display of a first personal digital assistant attached to the EKG electrodes such that a first responder views the EKG signals only on a display of the personal digital assistant;
    transmitting EKG measurement from the personal digital assistant over a wireless network to a second personal digital assistant of an health care professional; and
    displaying the EKG measurements on the second personal digital assistant for the health care professional, such that the health care professional views the same EKG signals as on the display of the first personal digital assistant.

* * * * *